United States Patent [19]
Jones

[11] Patent Number: 5,470,722
[45] Date of Patent: Nov. 28, 1995

[54] METHOD FOR THE AMPLIFICATION OF UNKNOWN FLANKING DNA SEQUENCE

[75] Inventor: Douglas H. Jones, Iowa City, Iowa

[73] Assignee: University of Iowa Research Foundation, Oakdale, Iowa

[21] Appl. No.: 58,907

[22] Filed: May 6, 1993

[51] Int. Cl.$^6$ .............................. C12N 15/70; C12Q 1/68
[52] U.S. Cl. ................. 435/91.2; 435/6; 435/172.3
[58] Field of Search ..................... 435/91.2, 6, 172.3; 935/77, 78

[56] References Cited

U.S. PATENT DOCUMENTS 4,661,450  4/1987  Kemp et al. ..................... 435/172.3

OTHER PUBLICATIONS

Jones and Winistorfer, *Nucleic Acids Res.*, 20:595–600 (1992).
Jones and Winistorfer, *PCR Methods Applic.*, 2:197–203 (1993).

*Primary Examiner*—Margaret Parr
*Assistant Examiner*—Eggerton Campbell
*Attorney, Agent, or Firm*—Frederick W. Pepper

[57] ABSTRACT

A method that permits the rapid amplification of unknown DNA that flanks a known site, such that one can walk into an uncharacterized region of DNA. In this method, human genomic DNA is restriction enzyme digested and then ligated to a 5' phosphorylated-oligonucleotide so that the 5' end of each strand of genomic DNA is extended and phosphorylated. The phosphorylated-oligonucleotide is constructed to render 5' end extensions that are complementary to the known sequence. Following denaturation and re-annealing under dilute conditions that promote intrastrand annealing and under high stringency, only those DNA strands containing the known sequence will form a stem-loop structure with a recessed and phosphorylated 5' end, rendering a substrate for a subsequent heat-stable ligation reaction to another oligonucleotide. This second oligonucleotide is complementary to the sequence immediately adjacent to the phosphorylated-oligonucleotide high stringency annealing site. The heat-stable ligation reaction appends a known sequence to the DNA segments containing the two known contiguous DNA sequences used for oligonucleotide annealing. This heat-stable ligation of known sequence permits the subsequent highly specific amplification of the unknown flanking DNA.

29 Claims, 10 Drawing Sheets

4. Add primer 2 and dNTPs (Polymerase extension of primer 2).
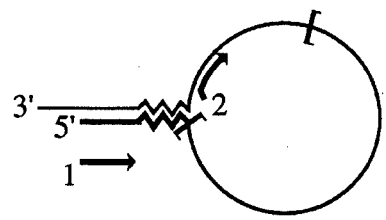
5. Thermal-cycle, resulting in DNA amplification.
6. Transfer an aliquot to an amplification mixture containing nested primers.
7. Thermal-cycle, resulting in DNA amplification.
Figure 1-2

4. Add dNTPs.

5. Thermal-cycle, resulting in DNA amplification.

6. Transfer an aliquot to an amplification mixture containing →

7. Thermal-cycle, resulting in DNA amplification.

8. Transfer an aliquot to an amplification mixture containing the phosphorylated-oligonucleotide.

9. Thermal-cycle, resulting in DNA amplification.

1. Restriction enzyme digest with an enzyme rendering a 5' overhang.
2. Ligate to ∿∿5'P using ∿∿5'P.
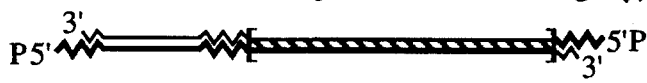
3. Add a thermal-stable DNA ligase and a thermal-stable DNA polymerase minus dNTPs.
↓ Denature
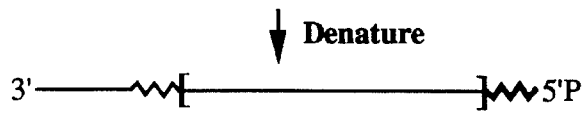
↓ Intra-strand anneal
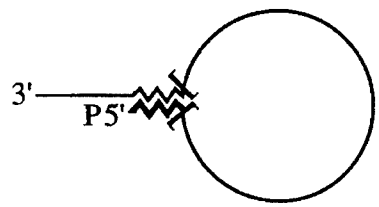
↓ Add excess ⟶ resulting in sequence specific ligation, and remaining free oligonucleotide.
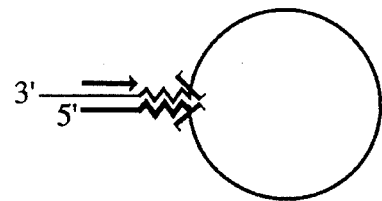
Figure 3-1

4. Add dNTPs.
5. Thermal-cycle, resulting in DNA amplification.
6. Transfer an aliquot to an amplification mixture containing the phosphorylated-oligonucleotide.
7. Thermal-cycle, resulting in DNA amplification.
Figure 3-2

METHOD FOR THE AMPLIFICATION OF UNKNOWN FLANKING DNA SEQUENCE

The U.S. Government has a paid-up license in this invention and the right in limited circumstances to require the patent owner to license others on reasonable terms as provided for by the terms of Grant No. R01HG00569 awarded by the National Institutes of Health.

FIELD OF THE INVENTION

The present invention relates to a method for the amplification of DNA. This method permits the amplification of an unknown DNA sequence that flanks a known DNA sequence. More particularly, this method eliminates the numerous steps and sequence artifacts associated with cloning. This method also permits genome walking into unclonable regions of DNA.

BACKGROUND OF THE INVENTION

The polymerase chain reaction (PCR) is a method which permits the specific in vitro amplification of DNA sequences [Mullis et al., *Cold Spring Hath. Syrup. Quant. Biol.*, 51:263–273 (1986); Saiki et al., *Science*, 239:487–491 (1988); Saiki et al., *Science*, 230: 1350–1354 (1985)]. PCR occurs by primer annealing to and extension from each end of a targeted sequence, and until recently has required knowledge of the primer annealing sites at each end of the targeted sequence. Recently, several methods have been developed for the amplification of unknown DNA that flanks one end of a known sequence, so that one may walk along a DNA sequence without screening a library for overlapping clones [Arnold & Hodgson, *PCR Methods Applic.*, 1: 39–42 (1991); Collasius et al., *J. Virol. Methods*, 32:115–119 (1991); Edwards et al., *Nucleic Acids Res.*, 19: 5227–5232 (1991); Fors et al., *Nucleic Acids Res.*, 18: 2793–2799 (1990); Frohman et al., *Proc. Natl. Acad. Sci.*, 85: 8998–9002 (1988); Gibbons, et al., *Proc. Natl. Acad. Sci.*, 88:8563–8567 (1991); Hovens and Wilks, *Nucleic Acids Res.*, 17:4415 (1989); Jones and Winistorfer, *Nucleic Acids Res.*, 20: 595–600 (1992); Jones and Winistorfer, *PCR Methods Applic.*, 2:197–203 (1993); Kandpal et al., *Nucleic Acids Res.*, 18:3081 (1990); Lagerstrom et al., *PCR Methods Applic.*, 1:111–119 (1991); Loh et al., *Science*, 243:2 17–220 (1989); MacGregor and Overbeek, *PCR Methods Applic.*, 1:129–135 (1991); Mueller and Wold, *Science*, 246:780–786 (1989); Ochman et al., *Genetics*, 120:621–623 (1988); Ohara et al., *Proc. Natl. Acad. Sci.*, 86:5673–5677 (1989); Parker et al., *Nucleic Acids Res.*, 19:3055–3060 (1991); Parks et al., *Nucleic Acids Res.*, 19:7155–7160 (1991); Pfeifer et al., *Science*, 246:810–813 (1989); Riley, et al., *Nucleic Acids Res.*, 18:2887–2890 (1990); Rosenthal and Jones, *Nucleic Acids Res.*, 18:3095–3096 (1990); Roux and Dhanarajan, *BioTechniques*, 8:48–57 (1990); Shyamala and Ames, *Gene*, 84:1–8 (1989); Silver and Keerikatte, *J. Virol.* 63:1924–1928 (1989); Triglia et al., *Nucleic Acids Res.*, 16:8186 (1988); Tormanen, et al., *Nucleic Acids Res.*, 20:5487–5488 (1992)].

A major obstacle in using existing methods for the PCR amplification of specific sequences in genomic DNA is the occurrence of nonspecific amplification products. Under PCR conditions, the stringency of the priming [Sommer and Tautz, *Nucleic Acids Res.*, 17:6749 (1989)] is seldom high enough to generate a pure product longer than 1 kilobase (kb) in highly complex mixtures, such as in human genomic DNA. This limits both the specificity of the reaction and the length of the amplifiable DNA. Use of nested primers [Mullis et al., *Cold Spring Harbor Symposia on Quantitative Biology, Cold Spring Harbor Laboratory*, L1:263–273 (1986); Haqqi et al., *Nucleic Acids Res.*, 16:11844 (1988)] and size selection of the regions of interest by previous Southern blotting [Ochman et al., *Genetics*, 120:621–623 (1988); Beck and Ho, *Nucleic Acids Res.*, 16:9051 (1988)] diminish this problem. However, high background due to insufficient stringency during the PCR amplification of genomic DNA remains a significant problem. It is not surprising, therefore, that the methods to amplify unknown flanking DNA result in limited specificity, as the initial PCR amplification using these methods does not improve upon the specificity level conferred by conventional two primer PCR. Certainly, an approach that optimizes the specificity of amplification is advantageous, regardless of the other strategies used to increase specificity (nested primers, size selection, physical separation of biotinylated products with steptavidin).

One method that has permitted the highly specific amplification of >2 kb of unknown DNA that flanks a known sequence from bulk human genomic DNA is panhandle PCR [Jones and Winistorfer, *Nucleic Acids Res.*, 20:595–600 (1992); Jones and Winistorfer, *PCR Methods Applic.*, 2:197–203 (1993)]. This method involves a primer dependent attachment of a known sequence to the uncharacterized side of a specific DNA strand which contains an unknown sequence. This permits specific PCR amplification of the unknown DNA because known sequence now flanks the strand that contains the unknown DNA. The PCR template is generated in the following manner. First, a restriction enzyme digests DNA leaving a 5' overhang. Second, a single-stranded oligonucleotide is ligated to the restriction enzyme digested DNA resulting in the modification of the 3' end of each strand. This oligonucleotide is constructed to be complementary to the known region of DNA immediately upstream from the unknown region of DNA. Third, denaturation and self-annealing under dilute conditions results in strands of DNA, containing the complement to the ligated piece, forming a single-stranded loop, or pan portion, with a double-stranded stem of an otherwise single-stranded handle, of a panhandle structure. The sequence specific annealing that constitutes the double-stranded stem can prime template-directed DNA polymerization from the ligated oligonucleotide. This polymerization results in known DNA being placed on the uncharacterized end of the unknown DNA contained in the loop. Generation of the panhandle template permits PCR amplification of the unknown DNA because known sequence now flanks the unknown DNA in those strands that contain the unknown DNA. However, in the panhandle PCR method, the initial priming during the amplification reaction must compete with intra-strand annealing of a long inverted repeat that comprises the handle of the panhandle template, which diminishes the efficiency of this necessary first step.

The present invention provides a method that permits the highly specific amplification of >2 kb of DNA that flanks the primer annealing sites from bulk human genomic DNA.

SUMMARY OF THE INVENTION

The present invention comprises a method that permits the rapid amplification of unknown DNA that flanks a known site, such that one can walk into an uncharacterized region of DNA. This method eliminates the numerous steps and sequence artifacts associated with cloning, and permits genome walking into unclonable regions of DNA. In this method, human genomic DNA is restriction enzyme digested and then ligated to a 5' phosphorylated-oligonucleotide so that the 5' end of each strand of genomic DNA is extended and phosphorylated. The phosphorylated-oligonucleotide is constructed to render 5' end extensions that are complementary to the known sequence. Following denaturation and re-annealing under dilute conditions that promote intrastrand annealing and under high stringency, only those DNA strands containing the known sequence will form a stem-loop structure with a recessed and phosphorylated 5' end, rendering a substrate for a subsequent heat-stable ligation reaction to another oligonucleotide. This second oligonucleotide is complementary to the sequence immediately adjacent to the phosphorylated-oligonucleotide high stringency annealing site. The heat-stable ligation reaction appends a known sequence to the DNA segments containing the two known contiguous DNA sequences used for oligonucleotide annealing. This heat-stable ligation of known sequence permits the subsequent highly specific amplification of the unknown flanking DNA. Therefore, this method requires the generation of a short inverted repeat of a portion of the known sequence on the unknown end of only those segments that contain the known sequence. Since the creation of this short inverted repeat is restricted to the targeted strand, and the presence of this inverted repeat is required for polymerase mediated amplification of the unknown flanking DNA, this method is termed targeted inverted repeat amplification.

In one embodiment, the invention relates to a method for amplification of an unknown DNA sequence that flanks a known DNA sequence, comprising the steps of:

(a) digesting a double-stranded DNA fragment with a restriction enzyme to yield 5' phosphorylated nucleotide overhang sequences, wherein said DNA fragment comprises a region of known DNA sequence and a region of unknown flanking DNA sequence to be amplified;

(b) annealing a 5' phosphorylated single-stranded oligonucleotide to a bridging-oligonucleotide to yield a double-stranded oligonucleotide with a phosphorylated 5' end;

(c) ligating said 5' phosphorylated single-stranded oligonucleotide of said double-stranded oligonucleotide whose non-phosphorylated 5' end is complementary to the cohesive ends generated in step (a) of said double-stranded DNA fragment to yield 5' phosphorylated nucleotide sequences complementary to a sequence portion within said known sequence region of said DNA fragment, wherein said sequence portion is an annealing site for said 5' phosphorylated nucleotide sequences;

(d) denaturing said 5' end-modified DNA fragment to produce single-stranded fragments containing said 5' phosphorylated nucleotide sequences;

(e) intra-strand annealing of a 5' phosphorylated nucleotide sequence to said annealing site within said known sequence region of a single-stranded fragment, wherein said single-stranded fragment is a fragment containing said annealing site located downstream (3') to said unknown flanking sequence region, to form a single-stranded loop, or pan portion, with a double-stranded stem of an otherwise single-stranded handle, of a panhandle structure;

(f) ligating an oligonucleotide primer 1, complementary to a known sequence region downstream (3') from said annealing site for said 5' phosphorylated nucleotide sequences, to the recessed 5' phosphorylated end of said double-stranded portion of said handle to elongate said double-stranded portion of said otherwise single-stranded handle of said panhandle structure;

(g) performing a first stage polymerase amplification reaction using a first set of oligonucleotide primers including said primer 1 annealing to said known sequence region downstream (3') from said annealing site for said 5' phosphorylated nucleotide sequences and a primer 2 complementary to a known sequence region both downstream (3') from said unknown flanking sequence region and upstream (5') from said annealing site for said 5' phosphorylated nucleotide sequences; and In another embodiment, the invention relates to a method for amplification of an unknown DNA sequence that flanks a known DNA sequence, which method comprises step (a) to (g) mentioned above; and further performing a second stage polymerase amplification reaction to produce a nested primer product using a second set of oligonucleotide primers including a primer 3 complementary to both a portion of said known sequence region complementary to primer 1 and a portion of said annealing site for said 5' phosphorylated nucleotide sequences and a primer 4 complementary to a known sequence region both downstream (3') from said unknown flanking sequence region and upstream (5') from said known sequence region complementary to primer 2.

In another embodiment, the invention relates to a method for amplification of an unknown DNA sequence that flanks a known DNA sequence, comprising the steps of:

(a) digesting a double-stranded DNA fragment with a restriction enzyme to yield 5' phosphorylated nucleotide overhang sequences, wherein said DNA fragment comprises a region of known DNA sequence and a region of unknown flanking DNA sequence to be amplified;

(b) annealing a 5' phosphorylated single-stranded oligonucleotide to a bridging-oligonucleotide to yield a double-stranded oligonucleotide with a phosphorylated 5' end;

(c) ligating said 5' phosphorylated single-stranded oligonucleotide of said double-stranded oligonucleotide whose non-phosphorylated 5' end is complementary to the cohesive ends generated in step (a) of said double-stranded DNA fragment to yield 5' phosphorylated nucleotide sequences complementary to a sequence portion within said known sequence region of said DNA fragment, wherein said sequence portion is an annealing site for said 5' phosphorylated nucleotide sequences;

(d) denaturing said 5' end-modified DNA fragment to produce single-stranded fragments containing said 5' phosphorylated nucleotide sequences;

(e) intra-strand annealing of a 5' phosphorylated nucleotide sequence to said annealing site within said known sequence region of a single-stranded fragment, wherein said single-stranded fragment is a fragment containing said annealing site located downstream (3') to said unknown flanking sequence region, to form a single-stranded loop, or pan portion, with a double-stranded stem of an otherwise single-stranded handle, of a panhandle structure;

(f) ligating an oligonucleotide primer 1, complementary to a known sequence region downstream (3') from said annealing site for said 5' phosphorylated nucleotide sequences, to the recessed 5' phosphorylated end of said double-stranded portion of said handle to elongate said double-stranded portion of said otherwise single-stranded handle of said panhandle structure;

(g) performing a first stage polymerase amplification reaction using said oligonucleotide primer 1 annealing to said known sequence region downstream (3') from said annealing site for said 5' phosphorylated nucleotide sequences;

(h) further performing a second stage polymerase chain reaction using an oligonucleotide primer 3 complementary to both a portion of said known sequence region complementary to primer 1 and a portion of said annealing site for said 5' phosphorylated nucleotide sequences; and (i) further performing a third stage polymerase chain reaction using an oligonucleotide primer complementary to said annealing site for said 5' phosphorylated nucleotide sequences.

In yet another embodiment, the invention relates to a method for amplification of an unknown DNA sequence that flanks a known DNA sequence, comprising the steps of:

(a) digesting a double-stranded DNA fragment with a restriction enzyme to yield 5' phosphorylated nucleotide overhang sequences, wherein said DNA fragment comprises a region of known DNA sequence and a region of unknown flanking DNA sequence to be amplified;

(b) annealing a 5' phosphorylated single-stranded oligonucleotide to a bridging-oligonucleotide to yield a double-stranded oligonucleotide with a phosphorylated 5' end;

(c) ligating said 5' phosphorylated single-stranded oligonucleotide of said double-stranded oligonucleotide whose non-phosphorylated 5' end is complementary to the cohesive ends generated in step (a) of said double-stranded DNA fragment to yield 5' phosphorylated nucleotide sequences complementary to a sequence portion within said known sequence region of said DNA fragment, wherein said sequence portion is an annealing site for said 5' phosphorylated nucleotide sequences;

(d) denaturing said 5' end-modified DNA fragment to produce single-stranded fragments containing said 5' phosphorylated nucleotide sequences;

(e) intra-strand annealing of a 5' phosphorylated nucleotide sequence to said annealing site within said known sequence region of a single-stranded fragment, wherein said single-stranded fragment is a fragment containing said annealing site located downstream (3') to said unknown flanking sequence region, to form a single-stranded loop, or pan portion, with a double-stranded stem of an otherwise single-stranded handle, of a panhandle structure;

(f) ligating an oligonucleotide primer 1, complementary to a known sequence region downstream (3') from said annealing site for said 5' phosphorylated nucleotide sequences, to the recessed 5' phosphorylated end of said double-stranded portion of said handle to elongate said double-stranded portion of said otherwise single-stranded handle of said panhandle structure;

(g) performing a first stage polymerase amplification reaction using said oligonucleotide primer 1 annealing to said known sequence region downstream (3') from said annealing site for said 5' phosphorylated nucleotide sequences; and (h) further performing a second stage polymerase amplification reaction using an oligonucleotide primer complementary to said annealing site for said 5' phosphorylated nucleotide sequences.

In yet another embodiment, the invention relates to a method for amplification of an unknown DNA sequence that flanks a known DNA sequence, comprising the steps of:

(a) digesting a double-stranded DNA fragment with a restriction enzyme to yield 3' nucleotide overhang sequences, wherein said DNA fragment comprises a region of known DNA sequence and a region of unknown flanking DNA sequence to be amplified;

(b) ligating a 5' phosphorylated single-stranded oligonucleotide whose 3' end is complementary to the cohesive ends generated in step (a) of said double-stranded DNA fragment to yield 5' phosphorylated nucleotide overhang sequences complementary to a sequence portion within said known sequence region of said DNA fragment, wherein said sequence portion is an annealing site for said 5' phosphorylated nucleotide overhang sequences;

(c) denaturing said 5' end-modified DNA fragment to produce single-stranded fragments containing said 5' phosphorylated nucleotide sequences;

(d) intra-strand annealing of a 5' phosphorylated nucleotide overhang sequence to said annealing site within said known sequence region of a single-stranded fragment, wherein said single-stranded fragment is a fragment containing said annealing site located downstream (3') to said unknown flanking sequence region, to form a single-stranded loop, or pan portion, with a double-stranded stem of an otherwise single-stranded handle, of a panhandle structure;

(e) ligating an oligonucleotide primer 1, complementary to a known sequence region downstream (3') from said annealing site for said 5' phosphorylated nucleotide overhang sequences, to the recessed 5' phosphorylated end of said double-stranded portion of said handle to elongate said double-stranded portion of said otherwise single-stranded handle of said panhandle structure;

(f) performing a first stage polymerase amplification reaction using a first set of oligonucleotide primers including said primer 1 annealing to said known sequence region downstream (3') from said annealing site for said 5' phosphorylated nucleotide overhang sequences and a primer 2 complementary to a known sequence region both downstream (3') from said unknown flanking sequence region and upstream (5') from said annealing site for said 5' phosphorylated nucleotide sequences; and (g) further performing a second stage polymerase amplification reaction to produce a nested primer product using a second set of oligonucleotide primers including a primer 3 complementary to both a portion of said known sequence region complementary to primer 1 and a portion of said annealing site for said 5' phosphorylated nucleotide sequences and a primer 4 complementary to a known sequence region both downstream (3') from said unknown flanking sequence region and upstream (5') from said known sequence region complementary to primer 2.

An object of the present invention is to develop a method that permits the PCR amplification and large-scale sequencing of unknown DNA flanking a known site in human genomic DNA.

Another object of the present invention is to develop a superior method for the construction of overlapping sets of cloned DNA.

Thus, the present invention overcomes major obstacles in the human genome project and has a myriad of applications in molecular biology, including: determination of viral integration sites, determination of transposon integration sites, amplification of fragments adjacent to cDNA such as regulatory regions and intron-exon junctions, generation of yeast artificial chromosome (YAC) [Burke et al., *Science, 236:* 806–812 (1987)] endpoints, and chromosome jumping [Collins et al., *Proc. Natl. Acad. Sci. USA.*, 81:6812–6816 (1984); Poustka et al., *Trends in Genet.*, 2:174–179 (1986)].

BRIEF DESCRIPTION OF THE DRAWINGS

These and various other objects, features, and many of the attendant advantages of the invention will be better understood upon a reading of the following detailed description when considered in connection with the accompanying drawings wherein:

FIG. 3 is a schematic representation of the targeted inverted repeat amplification in its third embodiment. The numbered steps correspond to the numbered steps in Methods. The two complementary strands of genomic DNA are thin and thick lines. DNA that flanks the known region of genomic DNA is enclosed by brackets and is striped when double-stranded. The phosphorylated-oligonucleotide is ᴡᴡ-5=P and the bridging-oligonucleotide is —ᴧ. The jagged portion of the thin line represents the annealing region for the ligated phosphorylated-oligonucleotide. Primers are arrows, and the phosphorylated-oligonucleotide is used as a primer. The location of the primers relative to the relevant strands of genomic DNA are shown on the top portion of step 1, and the primers are not added until later steps.

DETAILED DESCRIPTION OF THE INVENTION

Figure 1:
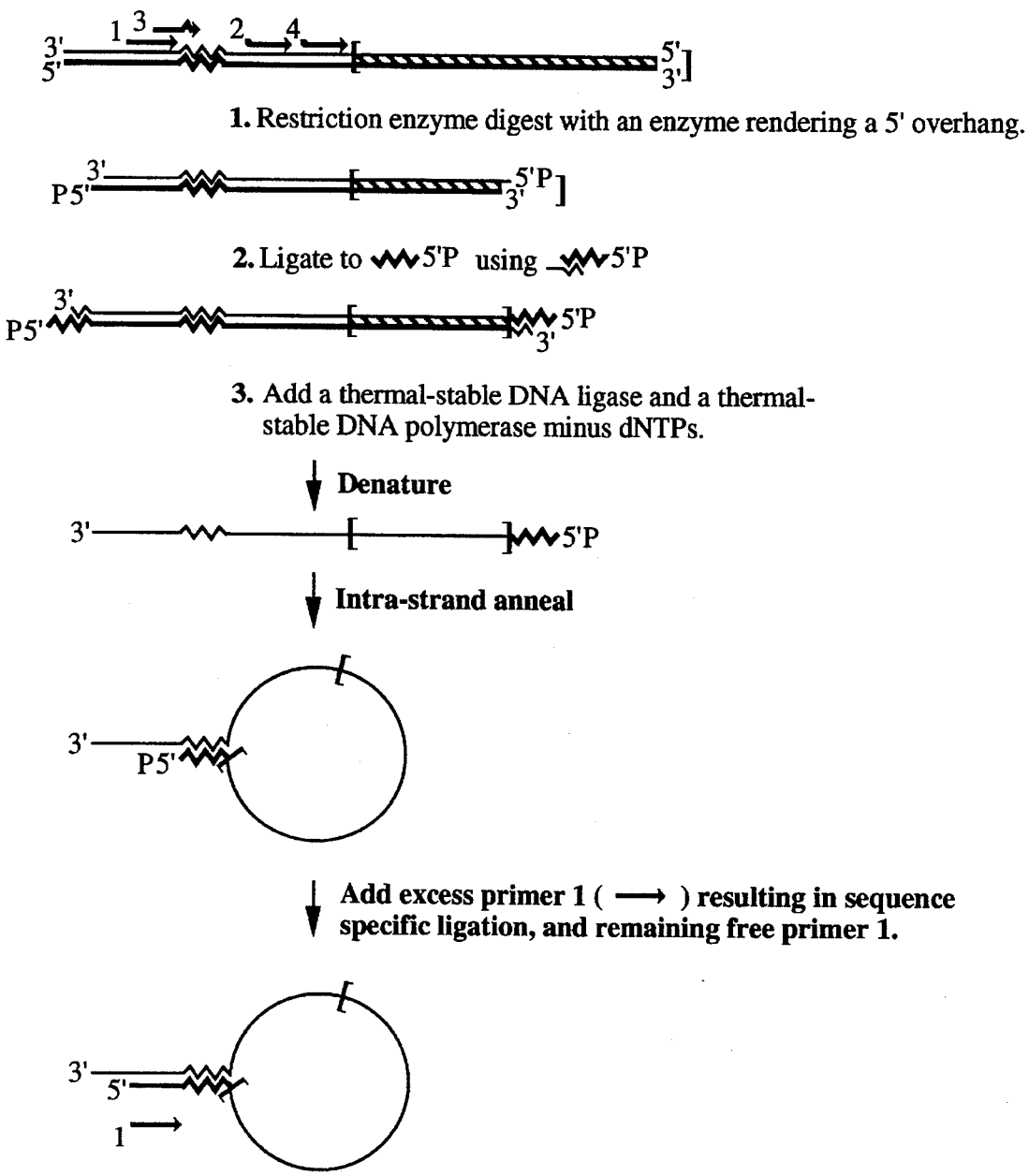
FIG. 1 is a schematic representation of the targeted inverted repeat amplification in its first embodiment. The two complementary strands of genomic DNA are thin and thick lines. DNA that flanks the known region of genomic DNA is enclosed by brackets and is striped when double-stranded. The phosphorylated-oligonucleotide is ~5 P and the bridging-oligonucleotide is —ᴧ. The jagged portion of the thin line represents the annealing region for the ligated phosphorylated-oligonucleotide. Primers are numbered arrows. The location of the primers relative to the relevant strands of genomic DNA are shown on the top portion of step 1. Primer 1 is ligated to the phosphorylated-oligonucleotide in step 3, and is not used as a primer until step 5. Primer is not added until step 4. Primers 3 and 4 are the nested primers, and are not added until step 6. One to five nucleotides are added to the 5' ends of primers 2 and 4 that are not complementary to their template, and are represented by upended 5' ends.
Figures 1, 2:
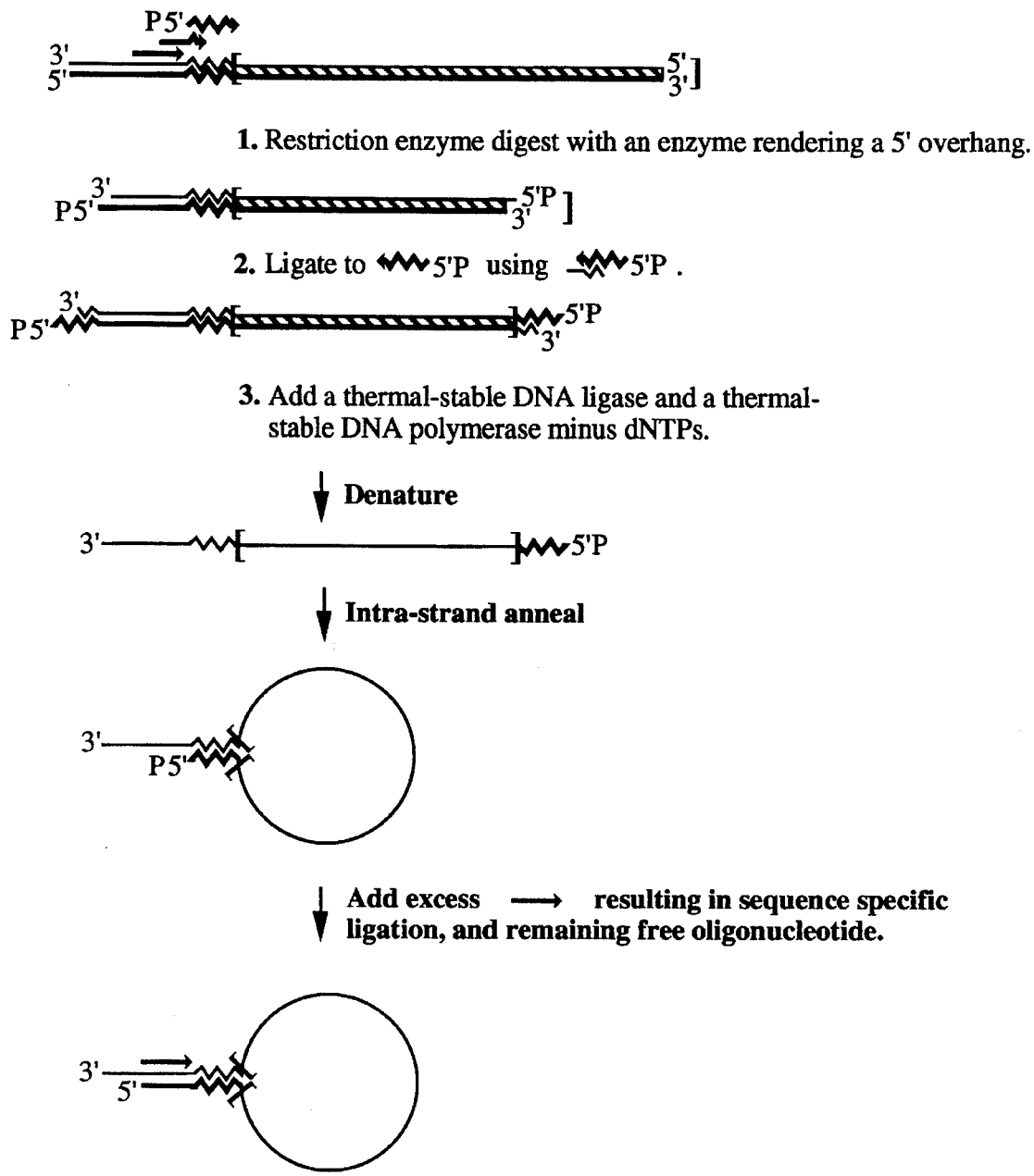
FIG. 2 is a schematic representation of the targeted inverted repeat amplification in its second embodiment. The two complementary strands of genomic DNA are thin and thick lines. DNA that flanks the known region of genomic DNA is enclosed by brackets and is striped when double-stranded. The phosphorylated-oligonucleotide is ᴡᴡ-5'P and the bridging-oligonucleotide is —ᴧ. The jagged portion of the thin line represents the annealing region for the ligated phosphorylated-oligonucleotide. Primers are arrows, and the phosphorylated-oligonucleotide is used as a primer. The location of the primers relative to the relevant strands of genomic DNA are shown on the top portion of step 1, and the primers are not added until later steps.
Figure 2:
Figure 2:
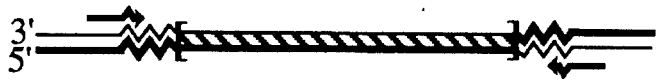
Figure 2:
Figure 2:
Figure 2:

Three embodiments of the targeted inverted repeat amplification are illustrated in FIGS. 1–3, respectively. The first manipulations are shared between the three embodiments (steps 1–4 in each of FIGS. 1–3), and are described briefly as follows: Human genomic DNA is digested with a restriction enzyme that renders a 5' overhang. These 5' ends are ligated to a 5' phosphorylated single-stranded oligonucleotide by using a non-phosphorylated bridging-oligonucleotide to juxtapose the 3' end of the phosphorylated-oligonucleotide to the restriction enzyme digested genomic DNA. The 5' ends of genomic DNA are extended by this ligation reaction using T4 DNA ligase. The phosphorylated-oligonucleotide that is ligated to the 5' ends of the human genomic DNA is complementary to a region of known DNA which is downstream, located 3', to the unknown region of interest. Following this ligation reaction, the complex mixture undergoes denaturation and annealing under dilute conditions that promote intra-strand annealing, and under high stringency so that those single strands of genomic DNA which contain the complement to the ligated phosphorylated-oligonucleotide form a stem-loop structure. This stem-loop structure has a recessed phosphorylated 5' end that renders a substrate for a site-specific ligation reaction of a second oligonucleotide using a heat-stable ligase. The heat-stable ligation reaction requires the sequence specific and adjacent annealing of two oligonucleotides, the phosphorylated-oligonucleotide that was ligated to the 5' ends of the restriction enzyme digested genomic DNA, and another oligonucleotide that is complementary to the known DNA immediately adjacent to the annealing site for the phosphorylated-oligonucleotide. This template differs from the panhandle PCR template because this initial template has a short inverted repeat, as opposed to the typically long inverted repeat in the panhandle amplification method [Jones and Winistorfer, *Nucleic Acids Res.*, 20:595–600 (1992)]. Furthermore, the generation of the final template with inverted repeats in this method entails a novel application of a heat-stable ligase [Barany, *Proc. Natl. Acad. Sci.*, 88:189–193 (1991); Landegren et al.,

*Science*, 241:1077–1080 (1988)].

The oligonucleotide appended to the phosphorylated oligonucleotide by the heat-stable ligase can, when present in its free, non-ligated form, prime an amplification reaction in those strands modified by the site-specific ligation of this same oligonucleotide. This oligonucleotide is designated as primer 1 in FIG. 1 and in Table 1 below.

TABLE 1. Oligonucleotides used to retrieve human genomic DNA flanking 5' end of the human cystic fibrosis transmembrane conductance regulator (CFTR) cDNA Bridging-oligonucleotide used to juxtapose phosphorylated-oligonucleotide to Hind III digested genomic DNA: AGCTGCTTGAGCCCAGAC. Annealing site to Hind III cut genomic DNA underlined).

Bridging oligonucleotide used to juxtapose phosphorylated-oligonucleotide to Xba I digested genomic DNA: CTAGGCTTGAGCCCAGAC. (Annealing site to Xba I cut genomic DNA underlined).

Phosphorylated-oligonucleotide ligated to Hind III or Xba I digested genomic DNA: 5' p-GTCCCTGCTAGGGC-CGTCTGGGCTCAAGC (SEQ ID No:3). Tm: 73.8° C.

Other oligonucleotides:

Primer 1: CCTCTGCATGGTCTCTCGGGCGCTGGG (SEQ ID No:4). Tm: 74.4° C.

Primer 2: TGAGGTAATGCCAAAGACCTACTACTCTGGG TGCCTGCCGC (SEQ ID No:5). 5' nucleotides not complementary to CFTR underlined; Tm: 77.8° C. Tm minus 5' TGAGG: 74.2° C.

Primer 3: TGGTCTCTCGGGCGCTGGGGTCCCTG (SEQ ID No:6). Tm: 74.9° C.

Primer 4: CCCGCTCAACCCTTTTTCTCTGACCTGCTGTG ATGTC (SEQ ID No:7). 5' nucleotide not complementary to CFTR underlined; Tm: 75.6° C., Tm minus 5' C: 74.0° C.).

Amplification using primer 1 alone is less efficient than amplification using primers 1 and 2, presumably due to competition with primer 1 annealing by snapback intrastrand annealing of the inverted repeat sequence. Therefore, the second and third embodiments, which use single primers during each DNA polymerase amplification step, require a larger number of total amplification cycles than the first embodiment (illustrated in FIG. 1), which uses two primers during each DNA polymerase amplification step. In the first embodiment, two primers are used during the DNA polymerase amplification steps. In this embodiment, one to five nucleotides are attached to the 5' end primers 2 and 4 that do not anneal to the original template. This is done, as a precaution, in order to prevent "short-circuiting" of the amplification reaction. Such short-circuiting can occur by annealing of the 3' end of a strand of a short non-specific amplification product (this strand being complementary to the strand into which primer 2 or 4 were incorporated) to the desired product, resulting in a short non-specific product.

Despite the diminished amplification yield when using a single primer instead of two primers, such amplification is highly specific, and renders the sequence of interest. In the second embodiment amplification with primer 1 is followed by a nested amplification using primer 3, which is then followed by third DNA amplification step using the phosphorylated-oligonucleotide (the phosphorylated 5' end serving no function during the amplification). In the third embodiment, amplification with primer 1 is followed by a single nested amplification using the phosphorylated-oligonucleotide.

Several steps are taken in order to simplify and optimize this method. The heat stable ligation reaction in step 3 of each protocol occurs in Taq polymerase buffer that is reconstituted with NAD. Heat-stable ligation using Ampligase is efficient in this buffer, and the NAD does not interfere with subsequent Taq polymerase mediated DNA amplification. This permits both the heat-stable ligation reaction and the DNA amplification to take place in the same buffer. High specificity and yield are obtained by utilizing a hot-start strategy prior to the heat stable ligation step and in all of the amplification steps in the first embodiment (in the second and third embodiments, the reactants are maintained at 4° C. prior to the final amplification step). A hot-start is accomplished by not allowing the temperature of the fully constituted heat-stable ligation or polymerase reactants to drop below 80° C. prior to an oligonucleotide annealing step, this temperature being well above the Tm of any of the oligonucleotides participating in the heat stable ligation reaction or being used as primers. The hot start eliminates ligation or priming at low stringency, and was developed to prevent the generation of unwanted products [Mullis, *PCR Methods Applic.*, 1:1–4 (1991)]. The Tm values for the annealing of oligonucleotides are calculated, and annealing temperatures are set at approximately 2°–4° C. below the Tm values.

Oligonucleotides are obtained from Midland Certified Reagent Company (Midland, Tex.). Phosphorylated 5' ends are generated by addition of a phosphorylated phosphoramidite during oligonucleotide synthesis. Oligonucleotide sequences and Tm values are in Table 1. Tm values are calculated using OLIGO 3.4 (National BioSciences, Hamel, N. Mex.).

Restriction enzyme digestion, as shown in step 1 of FIGS. 1, 2, and 3, is accomplished through the following procedure. Five μg of human genomic DNA (Clontech, Palo Alto, Calif.) is digested with 40 U of the restriction enzyme Hind III or Xba I (New England BioLabs, Beverly, Mass.) in 100 μl for two hours using the buffer supplied by the manufacturer.

Ligation of phosphorylated oligonucleotide, as shown in step 2 of FIGS. 1, 2, and 3, is carried out according to the following procedure. A 50-fold molar excess of the phosphorylated-oligonucleotide is ligated to 2.5 μg of genomic DNA (which has been cut to an average size of approximately 4 kb pieces by the 6 bp cutter in Step 1) as follows: The phosphorylated-oligonucleotide is annealed to an equal molar quantity of the bridging-oligonucleotide (this bridging oligonucleotide being constructed to juxtapose the 3' end of the phosphorylated-oligonucleotide to the 5' end of restriction enzyme digested genomic DNA), the genomic DNA is added, and ligation is accomplished by adding one unit of T4 DNA ligase (Boehringer Mannheim Biochemicals, Indianapolis, Ind.) and final 1 mM ATP, in 2x restriction enzyme buffer. Following incubation×1 hour at room temperature, 20 U of the restriction enzyme (Hind III or Xba I) is added and the tube is incubated at 37° C.×30 min. The ligated-oligonucleotide does not reconstitute a complete restriction enzyme recognition site for either of these restriction enzymes, so that only the restriction enzyme sites that have not been ligated to the oligonucleotide are digested. The reaction mix is allowed to cool to room temperature, 1 U of T4 DNA ligase is added and the tube is incubated at room temperature for 2 hours. The reaction mix then undergoes two rounds of glass-bead extraction using Geneclean (BIO 101, La Jolla, Calif.). Fifty μl of restriction enzyme digested genomic DNA that has not been ligated to the phosphorylated-oligonucleotide also undergoes Geneclean extraction× 2. Each Geneclean extracted sample is eluted in 25 μl TE (10 mM Tris-HCl pH 8, 1 mM EDTA).

The stem-loop formation and heat-stable oligonucleotide ligation, as represented in step 3 of FIGS. 1, 2, and 3, is as follows. Three tubes are used, each containing 2x PCR mix minus dNTPs in 25 µl (1.25 U Taq DNA polymerase (AmpliTaq, Perkin-Elmer Cetus, Norwalk, Conn.), 100 mM KCl, 20 mM Tris-HCl pH 8.3, 3 mM MgCl$_2$, 0.02% w/v gelatin). To each of these three tubes are added 10 µl H$_2$O, 5 µl of 6 mM NAD, and 1 µl containing 10 U of the heat-stable ligase Ampligase (Epicentre Technologies, Madison, Wis.). Fifty µl mineral oil is placed on top of each tube. These tubes are placed at 80° C., and 2 µl of undiluted template (from step 2) is added. The first tube receives restriction enzyme digested genomic DNA that has been ligated to the phosphorylated-oligonucleotide; the second tube receives restriction enzyme digested genomic DNA that has not been ligated to the phosphorylated-oligonucleotide; the third tube, a reagent control, does not receive any genomic DNA. The tubes undergo the following temperature transitions in a thermal cycler (Perkin Elmer Cetus original model) for stem-loop formation: 95° C.×1 min is followed by a 2 minute transition to 72° C.×15 min. Since the genomic DNA concentration is <4 ng/µl, the denaturation and re-annealing steps result in intra-strand annealing of the ligated phosphorylated-oligonucleotide to its complementary sequence in the genomic DNA [Triglia et al., *Nucleic Acids Res.*, 16:8186 (1988)]. When it first reaches 72° C., 12.5 pmoles of primer 1 in 5 µl is added to each tube, resulting in heat-stable ligation of primer 1 to the phosphorylated-oligonucleotide in the DNA strand (in tube 1) that has adjacent annealing sites for the ligated phosphorylated-oligonucleotide and primer 1.

The following refers to the first embodiment of the present invention which uses four primers with two primers in each of two DNA amplification reactions. The addition of primer 2 and of dNTPs, as shown in step 4 of FIG. 1, is accomplished through the following procedure. After 10 min at 72° C., 12.5 pmoles of primer 2 in 5 µl is added to each tube and 2 µl dNTPs are added (5 mM each dNTP, for a final concentration of 200 µM each dNTP). The addition of dNTPs renders a fully constituted polymerization mixture. The initial DNA amplification, as shown in step 5 of FIG. 1, is carried out according to the following procedure. The reactants undergo thermal-cycling using the following parameters: (95° C.×30 sec, 70° C.×30 sec, 72° C.×3 min)× 30 cycles are followed by incubation at 72° C.×7 min, and then transition to a 80° C. soak. The set up of nested DNA amplification, as represented in step 6 of FIG. 1, is as follows. One 1 µl is removed from each of the three tubes and placed in a corresponding second set of amplification reaction tubes that are reconstituted and placed at 80° C. as follows: Each amplification tube initially contains 2x PCR mix with dNTPs in 25 µl (1.25 U Taq DNA polymerase (AmpliTaq, Perkin-Elmer Cetus), 100 mM KCl, 20 mM Tris-HCl pH 8.3, 3 mM MgCl$_2$, 0.02% w/v gelatin, 400 µM each dNTP). Nineteen µl of H$_2$O is placed in each tube, 50 µl of mineral oil is layered on top, after which the tubes are placed at 80° C. and 12.5 pmoles of each nested primer (primer 3 and primer 4) in a total volume of 5 µl are added. For DNA amplification, as shown in step 7 of FIG. 1, the 3 new tubes undergo thermal-cycling using the following parameters: (95° C.×30 sec, 70° C.×30 sec, 72° C.×3 min)× 35 cycles followed by incubation at 72° C.×7 min.

The following refers to the second embodiment of the present invention which uses three primers with one primer in each of three DNA amplification reactions. The set up for single primer amplification (addition of dNTPs only; no addition of primer 2), as shown in step 4 of FIG. 2, is accomplished through the following procedure. After 15 min at 72° C. in Step 3, each tube undergoes denaturation at 95° C.×2 min. During this denaturation step, 2 µl dNTPs are added (5 mM each dNTP, for a final concentration of 200 µM each dNTP). The addition of dNTPs renders a fully constituted polymerization mixture. For this protocol, 15 µl instead of 10 µl of H$_2$O is added in Step 3. The initial DNA amplification, as shown in step 5 of FIG. 2, is carried out according to the following procedure. The reactants undergo thermal-cycling using the following parameters: (95° C.×30 sec, 70° C.×30 sec, 72° C.×3 min)×30 cycles followed by incubation at 72° C.×7 min, and then transition to a 80° C. soak. The set up of DNA amplification, as represented in step 6 of FIG. 2, is as follows. One µl is removed from each of the three tubes and placed in a corresponding second set of amplification reaction tubes that are reconstituted and placed at 80° C. as follows: Each amplification tube initially contains 2x PCR mix with dNTPs in 25 µl (1.25 U Taq DNA polymerase (AmpliTaq, Perkin-Elmer Cetus), 100 mM KCl, 20 mM Tris-HCl pH 8.3, 3 mM MgCl$_2$, 0.02% w/v gelatin, 400 µM each dNTP). Nineteen µl of H$_2$O is placed in each tube, 50 µl of mineral oil is layered on top, after which the tubes are placed at 80° C. and 12.5 pmoles of the nested primer (primer 3 only) in a total volume of 5 µl are added.

For DNA amplification, as shown in step 7 of FIG. 2, the 3 new tubes undergo thermal-cycling using the following parameters: (95° C.×30 sec, 70° C.×30 sec, 72° C.×3 min)× 35 cycles followed by incubation at 72° C.×7 min, and then transition to a 4° C. soak. The set up of DNA amplification, as represented in step 8 of FIG. 2, is as follows. One µl is removed from each of the three tubes and placed in a corresponding third set of amplification reaction tubes that are reconstituted and placed at 80° C. as follows: Each amplification tube initially contains 2x PCR mix with dNTPs in 25 µl (1.25 U Taq DNA polymerase (AmpliTaq, Perkin-Elmer Cetus), 100 mM KCl, 20 mM Tris-HCl pH 8.3, 3 mM MgCl$_2$, 0.02% w/v gelatin, 400 µM each dNTP). Nineteen µl of H$_2$O is placed in each tube, 50 µl of mineral oil is layered on top, after which the tubes are placed at 80° C. and 12.5 pmoles of the nested primer (the phosphorylated-oligonucleotide only) in a total volume of 5 µl are added. For DNA amplification, as shown in step 9 of FIG. 2, the 3 new tubes undergo thermal-cycling using the following parameters: (95° C.×30 sec, 70° C.×30 sec, 72° C.×3 min)×35 cycles followed by incubation at 72° C.×7 min.

The following refers to the third embodiment of the present invention which uses two primers with one primer in each of two DNA amplification reactions. The set up for single primer amplification (addition of dNTPs only; no addition of primer 2), as shown in step 4 of FIG. 3, is accomplished through the following procedure. After 15 min at 72° C. in Step 3, each tube undergoes denaturation at 95° C.×2 min. During this denaturation step, 2 µl dNTPs are added (5 mM each dNTP, for a final concentration of 200 µM each dNTP). The addition of dNTPs renders a fully constituted polymerization mixture. For this protocol, 15 µl instead of 10 µl of H$_2$O is added in Step 3. As shown in step 5 of FIG. 3, the reactants undergo thermal-cycling using the following parameters: (95° C.×30 sec, 70° C.×30 sec, 72° C.×3 min)×30 cycles followed by incubation at 72° C.×7 min, and then transition to a 80° C. soak. Then, the tubes undergo thermal-cycling using the following parameters: (95° C.×30 sec, 70° C.×30 sec, 72° C.×3 min)×35 cycles followed by incubation at 72° C.×7 min, and then transition to a 4° C. soak. (The total of 65 amplification cycles occur using primer 1 only). The set up of DNA amplification, as represented in step 6 of FIG. 3, is as follows. One µl is removed from each of the three tubes and placed in a corresponding second set of amplification reaction tubes that are reconstituted and placed at 80° C. as follows: Each amplification tube initially contains 2x PCR mix with dNTPs in 25 µl (1.25 U Taq DNA polymerase (AmpliTaq, Perkin-Elmer Cetus), 100 mM KCl, 20 mM Tris-HCl pH 8.3, 3 mM MgCl$_2$, 0.02% w/v gelatin, 400 µM each dNTP). Nineteen µl of H$_2$O is placed in each tube, 50 µl of mineral oil is layered on top, after which the tubes are placed at 80° C. and 12.5 pmoles of the nested primer (the phosphorylated-oligonucleotide only) in a total volume of 5 µl are added. For DNA amplification, as shown in step 7 of FIG. 3, the 3 new tubes undergo thermal-cycling using the following parameters: (95° C.×30 sec, 70° C.×30 sec, 72° C.×3 min)×35 cycles followed by incubation at 72° C.×7 min.

Nine µl of each PCR product are analyzed by agarose gel electrophoresis followed by ethidium bromide staining. PCR products are cloned into pUC19 using recombination PCR [Jones and Howard, *BioTechniques*, 10:62–66 (1991)]. pUC19 is digested with Hind III. Then 2 ng of the linearized pUC19 undergoes 20 cycles of PCR amplification using primers whose 5' ends have 24 nucleotides of complementary to the 5' ends of the primer(s) that are used in the final nested amplification in the targeted inverted repeat amplification method. This results in a vector with ends that are homologous to the final targeted inverted repeat amplification product. 2.5 µl of each of two crude amplification products: the PCR amplified and modified linear plasmid and the targeted inverted repeat amplification product are co-transfected into MAX efficiency (>1×10$^9$/µg monomer pUC19) DH5α competent *E. coli*(GIBCO BRL/Life Technologies, Gaithersburg, Md.). Transformed clones are grown overnight in LB broth at 37° C., and 2 µl of the growth, without boiling or extraction of plasmids, is screened for the recombinant by PCR amplification using M13 and RM13 primers followed by minigel analysis.

Plasmids are purified with Qiagen-tip 100 columns (Qiagen Inc., Studio City, Calif.). The ends of the plasmid inserts are sequenced by the dideoxy method [Sanger et al., *Proc. Natl. Acad. Sci.*, 74:5463–5467 (1977)] using Sequenase version 2.0 (United States Biochemical, Cleveland, Ohio). Sequencing reactions are primed with standard M13 and RM13 primers in order to identify the inserts.

The present invention differs from conventional PCR in three essential aspects:

1) The present invention is dependent upon a heat-stable ligation reaction in order for the polymerase-mediated amplification to occur.

2) The present invention generates an inverted repeat in a sequence dependent manner.

3) The 3' ends of the primers used in the present invention are oriented in the same direction on the original template, and are positioned on one side of the region that is to be amplified. In conventional PCR, the 3' ends of the primers are oriented in opposite directions on the original template.

It should be noted that any of these embodiments can be adapted in order to permit the purification of a sequence from a complex mixture. Prior to amplification, the inverted repeat structure, with extraneous strands, is suspended with a DNA polymerase that has 3' exonuclease activity with 1–4 dNTPs. Candidate polymerases are Vent polymerase (New England Biolabs) or Pfu DNA polymerase (Stratagene, La Jolla, Calif.). As the 3' exonuclease activity of the DNA polymerase removes single-stranded 3' DNA ends, the single-stranded loop region in the sequence of interest is protected by the double-stranded inverted repeat. This step will eliminate many of the sequences that are not of interest prior to a subsequent step, such as amplification.

The invention herein also contemplates a kit for DNA amplification or purification comprising a heat stable ligase, a heat stable DNA polymerase, and a single buffer that provides the proper environment for the heat stable ligase and the heat stable DNA polymerase.

One advantage of the present invention over the panhandle PCR method is shown by the first embodiment which uses four primers. In the first embodiment, the initial priming occurs following annealing of primer 2 to the single-stranded loop portion of the template. Therefore, this primer annealing does not need to compete with snapback intra-strand annealing by the inverted repeat and occurs efficiently. However, in the panhandle PCR method, the initial priming during the amplification reaction must compete with intra-strand annealing of a long inverted repeat that comprises the handle of the panhandle template, which diminishes the efficiency of this necessary first step. Also in the present invention, the same phosphorylated-oligonucleotide can be used with any restriction enzyme that renders a 5' overhang, and only the short bridging-oligonucleotide needs to be modified for different 5' overhangs generated by different restriction enzymes.

The second and third embodiments of the present invention use fewer number of primers and a shorter length of known sequence in order to amplify 2 kb of DNA that flanks a known sequence. Diminishing the length of known sequence necessary to amplify unknown flanking DNA is of particular value in amplifying a promoter from a cDNA when an intron lies near the 5' end of the cDNA. Each of these protocols uses a single primer during each DNA amplification step. Amplification with single primers is less efficient than with the two primers in the first embodiment of the present invention, so that a larger number of total amplification cycles is required than with the first embodiment, which uses two primers during each DNA amplification. Nevertheless, high specificity is retained, with considerable cost savings incurred by manufacturing fewer primers.

Applications of this present invention include chromosome walking, retrieval and sequencing of unclonable DNA, amplification of fragments adjacent to cDNA such as regulatory regions and intron-exon junctions, determination of the insertion sites of viruses, transposons, or other DNA fragments, the generation of yeast artificial chromosome (YAC) endpoints [Riley, et al., *Nucleic Acids Res.*, 18:2887–2890 (1990)], and detection of DNA sequences, such as for diagnostic purposes.

The above disclosure generally describes the present invention. A more complete understanding can be obtained by reference to the following specific examples which are proposed for purposes of illustration only, and are not intended to limit the scope of the invention.

EXAMPLE 1

Figure 4:
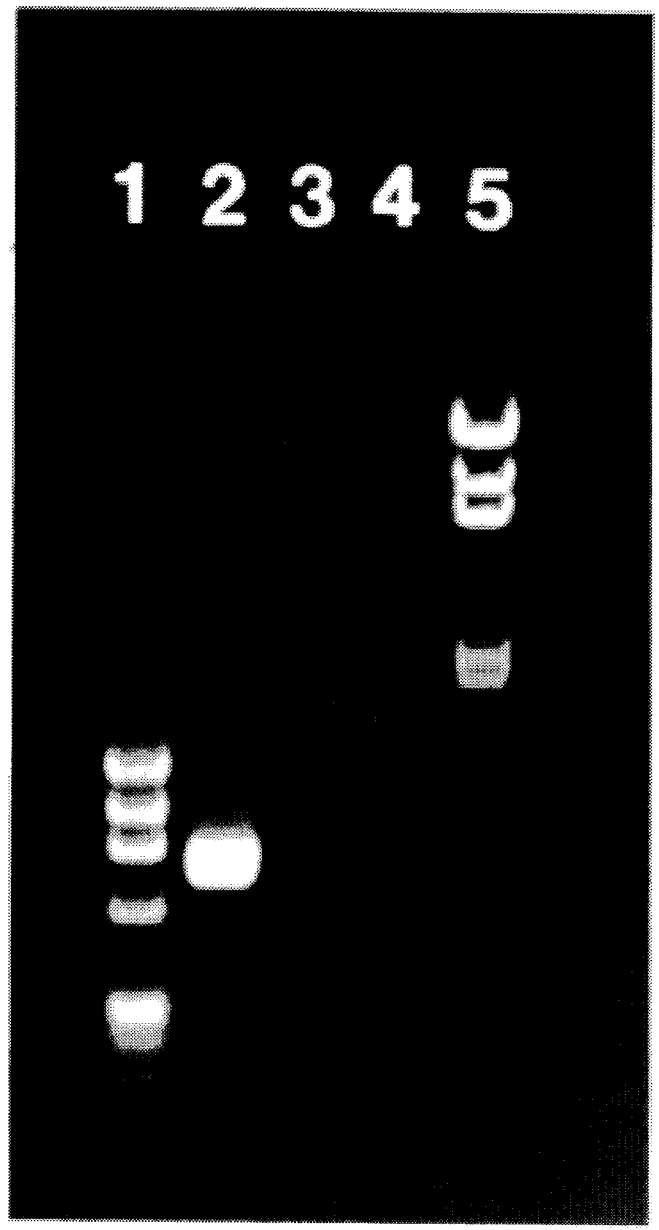
FIG. 4 shows the results of amplification of the DNA sequence 5' to the CFTR gene directly from human genomic DNA using a heat-stable ligation reaction and four DNA amplification primers, two primers in each of two DNA polymerase amplifications (first embodiment), run on an agarose gel.

Amplification of a 671 bp DNA Flanking the Primer Annealing Sites Using Targeted Inverted Repeat Amplification To amplify human genomic DNA that flanks the primer annealing sites, the G/C rich DNA sequence upstream to the human cystic fibrosis transmembrane conductance regulator (CFTR) cDNA was amplified using four amplification primers, resulting in a 756 bp DNA fragment containing 671 bp of DNA flanking the primer annealing sites (see FIG. 4). The DNA amplifications were carried out on bulk genomic DNA, and rendered the fragment of interest with high specificity. A control template and reagent control were also amplified. Nine μl of each of the three final products were run on a 1% agarose gel, and only the tube that initially contained the genomic DNA following restriction enzyme digestion (Hind III), ligation to the phosphorylated-oligonucleotide, and heat-stable ligation to primer 1 prior to the amplification reactions yielded a detectable product following ethidium bromide staining (see FIG. 4, lane 2). The product was obtained with high specificity, and was subcloned using the recombination PCR method [Jones and Howard, *BioTechniques*, 10:62–66 (1991)]. Sequencing of the insert ends of six clones revealed the product of interest [Yoshimura et al., *J. Biol. Chem.*, 266: 9140–9144 (1991); Zielenski et al., *Genomic*, 10: 214–228 (1991)].

EXAMPLE 2

Figure 5:
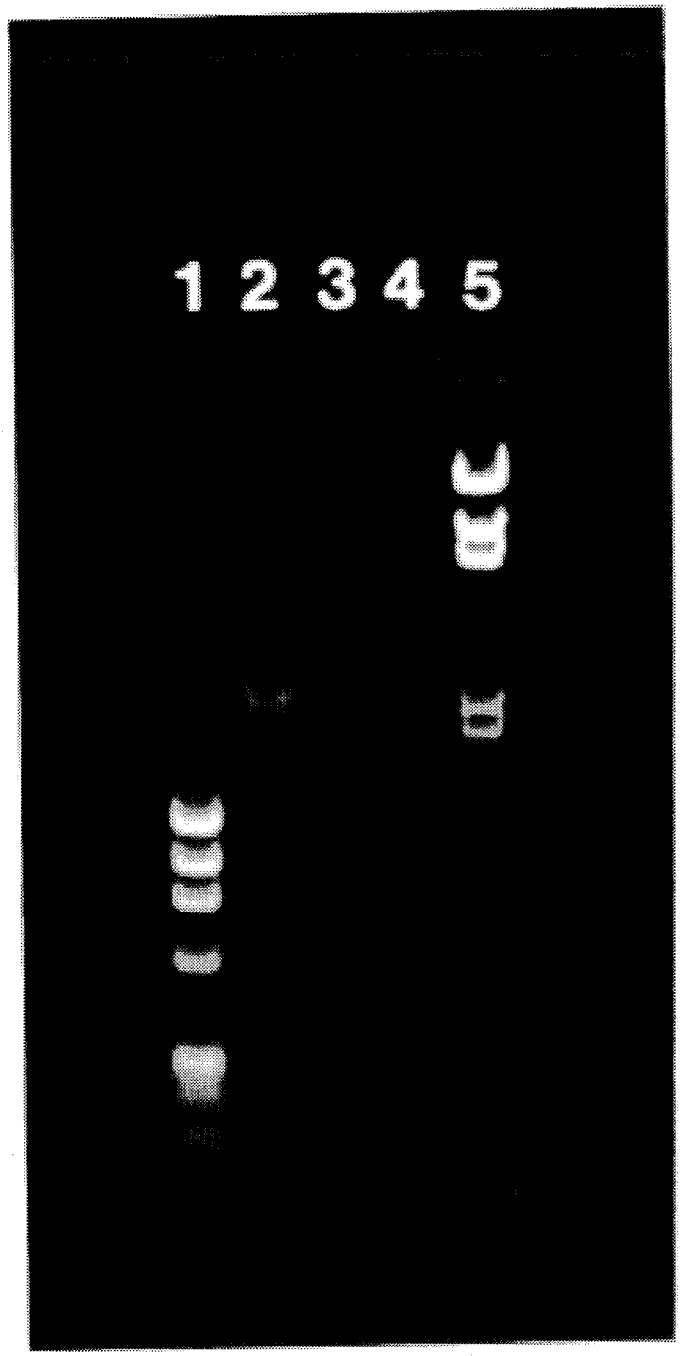
FIG. 5 shows the results of amplification of the DNA sequence 5' to the CFTR gene directly from human genomic DNA using a heat-stable ligation reaction and four DNA amplification primers, two primers in each of two DNA polymerase amplifications (first embodiment), run on an agarose gel.

Amplification of a 2.2 kb DNA Flanking the Primer Annealing Sites Using Targeted Inverted Repeat Amplification To amplify >2 kb of human genomic DNA that flanks the primer annealing sites, a longer DNA sequence upstream to the CFTR cDNA was amplified using four amplification primers, resulting in a 2286 bp DNA fragment containing 2201 bp of DNA flanking the primer annealing sites (see FIG. 5). The DNA amplifications were carried out on bulk genomic DNA, and rendered the fragment of interest with high specificity. A control template and reagent control were also amplified. Nine μl of each product was run on a 1% agarose gel, and only the tube that initially contained the genomic DNA following restriction enzyme digestion (Xba I), ligation to the phosphorylated-oligonucleotide, and heat-stable ligation to primer 1 prior to the amplification reactions yielded a detectable product following ethidium bromide staining (see FIG. 5, lane 2). The product was obtained with high specificity, and was subcloned using the recombination PCR method [Jones and Howard, *BioTechniques*, 10:62–66 (1991)]. Sequencing of the insert ends of six clones revealed the product of interest [Yoshimura et al., *J. Biol. Chem.*, 266:9140–9144 (1991); Zielenski et al., *Genomic*, 10:214–228 (1991)].

EXAMPLE 3

Figure 6:
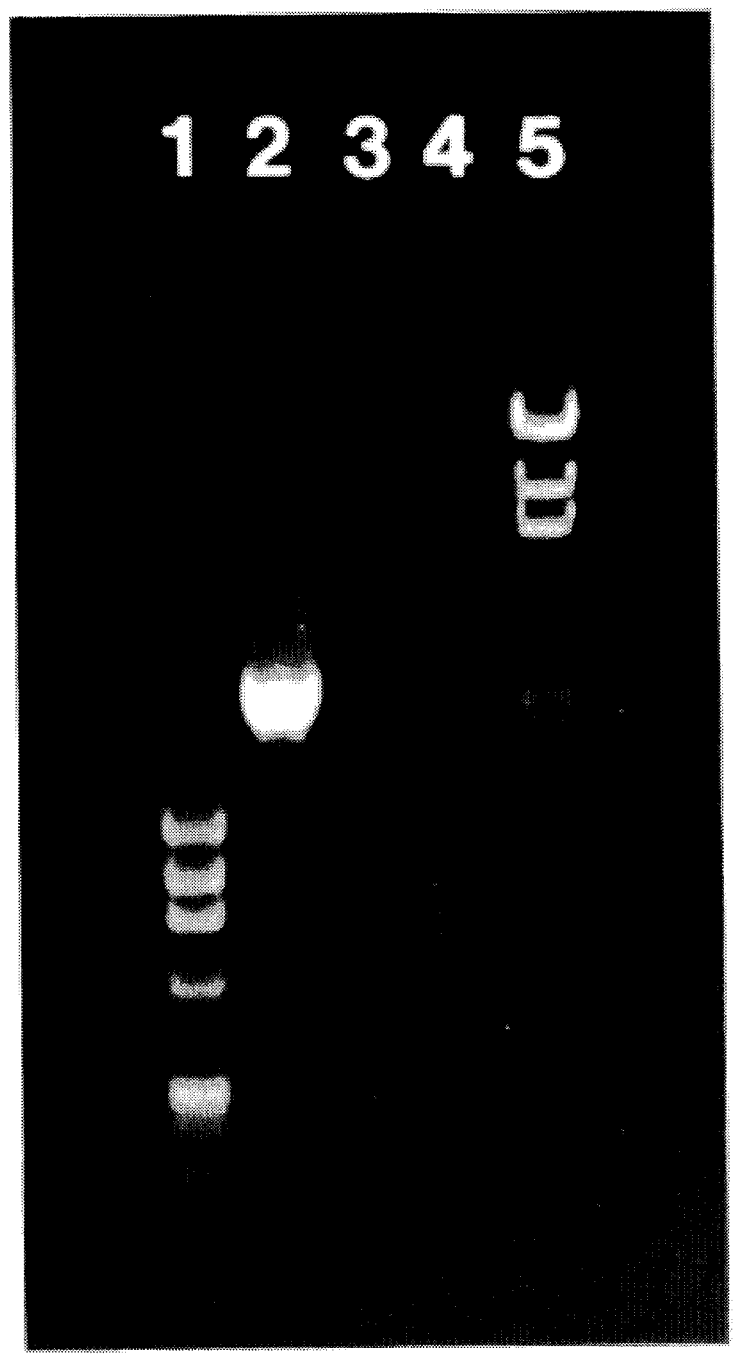
FIG. 6 shows the results of amplification of the DNA sequence 5' to the CFTR gene directly from human genomic DNA using a heat-stable ligation reaction and three DNA amplification primers (second embodiment), one primer in each of three DNA polymerase amplifications, run on an agarose gel.

Amplification of a 2.3 kb DNA Flanking the Primer Annealing Sites Using Targeted Inverted Repeat Amplification A 2.3 kb fragment was amplified lying upstream to the CFTR cDNA primer annealing sites using single primers during each amplification, in three sequential single primer amplification reactions. The three primers used in the second embodiment of the present invention (illustrated in FIG. 2), in order of use, are primers 1, 3, and the phosphorylated-oligonucleotide in Table 1. This resulted in a 2330 bp DNA fragment containing 2272 bp of DNA flanking the primer annealing sites (see FIG. 6). The DNA amplifications were carried out on bulk genomic DNA, and rendered the fragment of interest with high specificity. A control template and reagent control were also amplified. Nine μl of each product was run on a 1% agarose gel, and only the tube that initially contained the genomic DNA following restriction enzyme digestion (Xba I), ligation to the phosphorylated-oligonucleotide, and heat-stable ligation to primer 1 prior to the amplification reactions yielded a detectable product following ethidium bromide staining (see FIG. 6, lane 2). The product was obtained with high specificity, and was subcloned using the recombination PCR method [Jones and Howard, *BioTechniques*, 10:62–66 (1991)]. Sequencing of the insert ends of three clones revealed the product of interest [Yoshimura et al., *J. Biol. Chem.*, 266: 9140–9144 (1991); Zielenski et al., *Genomic*, 10:214–228 (1991)].

EXAMPLE 4

Figure 7:
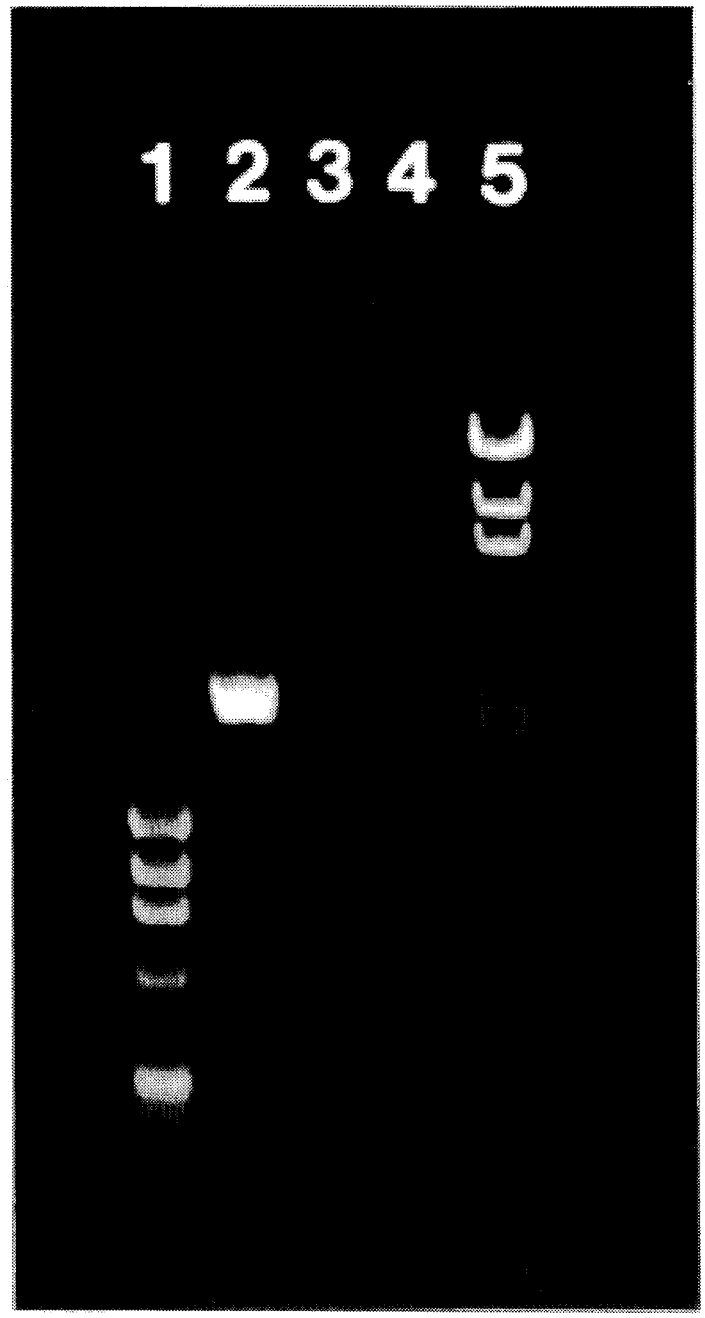
FIG. 7 shows the results of amplification of the DNA sequence 5' to the CFTR gene directly from human genomic DNA using a heat-stable ligation reaction and two DNA amplification primers (third embodiment), one primer in each of two DNA polymerase amplifications, run on an agarose gel.

Amplification of a 2.3 kb DNA Flanking the Primer Annealing Sites Using Targeted Inverted Repeat Amplification We next attempted to amplify the 2.3 kb fragment lying upstream to the CFTR cDNA primer annealing sites using single primers during each amplification, in two sequential single primer amplification reactions. The two primers used in third embodiment of the present invention (illustrated in FIG. 3), in order of use, are primer 1 and the phosphorylated-oligonucleotide in Table 1. This resulted in a 2330 bp DNA fragment containing 2272 bp of DNA flanking the primer annealing sites (see FIG. 7). The DNA amplifications were carried out on bulk genomic DNA, and rendered the fragment of interest with high specificity. A control template and reagent control were also amplified. Nine μl of each PCR product was run on a 1% agarose gel, and only the tube that initially contained the genomic DNA following restriction enzyme digestion (Xba I), ligation to the phosphorylated-oligonucleotide, and heat-stable ligation to primer 1 prior to the amplification reactions yielded a detectable product following ethidium bromide staining (see FIG. 7, lane 2). Less product was obtained using the third embodiment than was obtained using the second embodiment of the present invention. The product was subcloned using the recombination PCR method [Jones and Howard, *BioTechniques*, 10:62–66 (1991)]. Sequencing of the insert ends of three clones revealed the product of interest [Yoshimura et al., *J. Biol. Chem.*, 266:9140–9144 (1991); Zielenski et al., *Genomic*, 10:214–228 (1991)].

The invention now being fully described, it will be apparent to one of ordinary skill in the art that many changes and modifications can be made without departing from the spirit or scope of the invention.

What is claimed is:

1. A method for the amplification of an unknown DNA sequence that flanks a known DNA sequence, comprising the steps of:

(a) digesting a double-stranded DNA fragment with a restricuion enzyme to yield 5' phosphorylated nucleotide overhang sequences, wherein said DNA fragment comprises a region of known DNA sequence and a region of unknown flanking DNA sequence to be amplified;

(b) annealing a 5' phosphorylated single-stranded oligonucieotide to a bridging-oligonucleotide to yield a double-stranded oligonucleotide with a 5' phosphorylated end;

(c) ligating said 5' phosphorylated single-stranded oligonucleotide of said double-stranded oligonucleotide whose non-phosphorylated 5' end is complementary to the cohesive ends generated in step (a) of said double-stranded DNA fragment to yield 5' phosphorylated nucleotide sequences complementary to a sequence portion within said known sequence region of said DNA fragment, wherein said sequence portion is an annealing site for said 5' phosphorylated nucleotide sequences;

(d) denaturing said 5' end-modified DNA fragment to produce single-stranded fragments containing said 5' phosphorylated nucleotide sequences;

(e) intra-strand annealing of a 5' phosphorylated nucleotide sequence to said annealing site within said known sequence region of a single-stranded fragment, wherein said single-stranded fragment is a fragment containing said annealing site located downstream (3') to said unknown flanking sequence region, to form a single-stranded loop, or pan portion, with a double-stranded stem of an otherwise single-stranded handle, of a panhandle structure;

f) heat stable ligating an oligonucleotide primer 1, complementary to a known sequence region downstream (3') from said annealing cite for said 5' phosphorylated nucleotide sequences, to the recessed 5' phosphorylated end of said double-stranded portion of said handle to elongate said double-stranded portion of said otherwise single-stranded handle of said panhandle structure; and (g) performing a first stage polymerace amplification reaction using a first set of oligonucleotide primers including said primer 1 annealing to said known sequence region downstream (3') from said annealing site for said 5' phosphorylated nucleotide sequences and a primer 2 complementary to a known sequence region both downstream (3') from said unknown flanking sequence region and upstream (5') from said annealing site for said 5' phosphorylated nucleotide sequences wherein initial priming by primer 2 occurs following annealing to said pan portion of said panhandle structure and is not inhibited by snapback annealing of said double-stranded handle of said panhandle structure.

2. The method of claim 1, further performing a second stage polymerase amplification reaction to produce a nested primer product using a second set of oligonucleotide primers including a primer 3 complementary to both a portion of said known sequence region complementary to primer 1 and a portion of said annealing site for said 5' phosphorylated nucleotide sequences and a primer 4 complementary to a known sequence region both downstream (3') from said unknown flanking sequence region and upstream (5') from said known sequence region complementary to primer 2.

3. The method of claim 1, wherein said double-stranded DNA is genomic.

4. The method of claim 1, wherein said region of known sequence is an insertion element and said region of unknown flanking DNA sequence to be retrieved is an integration site for said insertion element and flanking regions thereof.

5. The method of claim 4, wherein said insertion element is a viral insertion element or a transposon insertion element.

6. The method of claim 1, wherein said region of known sequence is a cDNA and said region of unknown flanking DNA sequence to be retrieved is from a 3' or 5' flanking region, intron-exon junction, or intron.

7. The method of claim 1, wherein said region of known sequence is a cloning vector arm and said region of unknown flanking DNA sequence to be retrieved is the cloned DNA sequence lying adjacent said arm.

8. The method of claim 7, wherein said cloning vector is a yeast artificial chromosome.

9. The method of claim 1, wherein said double-stranded DNA is known.

10. The method of claim 1, wherein said double-stranded DNA is a gene, disease marker, or pathogen.

11. A method for the amplification of an unknown DNA sequence that flanks a known DNA sequence, comprising the steps of:
   (a) digesting a double-stranded DNA fragment with a restriction enzyme to yield 3' nucleotide overhang sequences, wherein said DNA fragment comprises a region of known DNA sequence and a region of unknown flanking DNA sequence to be amplified;
   (b) ligating a 5' phosphorylated single-stranded oligonucleotide whose 3' end is complementary to the cohesive ends generated in step (a) of said double-stranded DNA fragment to yield 5' phosphorylated nucleotide overhang sequences complementary to a sequence portion within said known sequence region of said DNA fragment, wherein said sequence portion is an annealing site for said 5' phosphorylated nucleotide overhang sequences;
   (c) denaturing said 5' end-modified DNA fragment to produce single-stranded fragments containing said 5' phosphorylated nucleotide sequences;
   (d) intra-strand annealing of a 5' phosphorylated nucleotide overhang sequence to said annealing site within said known sequence region of a single-stranded fragment, wherein said single-stranded fragment is a fragment containing said annealing site located downstream (3') to said unknown flanking sequence region, to form a single-stranded loop, or pan portion, with a double-stranded stem of an otherwise single-stranded handle, of a panhandle structure;
   (e) heat stable ligating an oligonucleotide primer 1, complementary to a known sequence region downstream (3') from said annealing site for said 5' phosphorylated nucleotide overhang sequences, to the recessed 5' phosphorylated end of said double-stranded portion of said handle to elongate said double-stranded portion of said otherwise single-stranded handle of said panhandle structure;
   (f) performing a first stage polymerase amplification reaction using a first set of oligonucleotide primers including said primer 1 annealing to said known sequence region downstream (3') from said annealing site for said 5' phosphorylated nucleotide overhang sequences and a primer 2 complementary to a known sequence region both downstream (3') from said unknown flanking sequence region and upstream (5') from said annealing site for said 5' phosphorylated nucleotide sequences wherein inital priming by primer 2 occurs following annealing to said pan portion of said panhandle structure and is not inhibited by snapback annealing of said double-stranded handle of said panhandle structure; and
   (g) further performing a second stage polymerase amplification reaction to produce a nested primer product using a second set of oligonucleotide primers including a primer 3 complementary to both a portion of said known sequence region complementary to primer 1 and a portion of said annealing site for said 5' phosphorylated nucleotide sequences and a primer 4 complementary to a known sequence region both downstream (3') from said unknown flanking sequence region and upstream (5') from said known sequence region complementary to primer 2.

12. A method for the amplification of an unknown DNA sequence that flanks a known DNA sequence, comprising the steps of:
   (a) digesting a double-stranded DNA fragment with a restriction enzyme to yield 5' phosphorylated nucleotide overhang sequences, wherein said DNA fragment comprises a region of known DNA sequence and a region of unknown flanking DNA sequence to be amplified;
   (b) annealing a 5' phosphorylated single-stranded oligonucleotide to a bridging-oligonucleotide to yield a double-stranded oligonucleotide with a phosphorylated 5' end;
   (c) ligating said 5' phosphorylated single-stranded oligonucleotide of said double-stranded oligonucleotide whose non-phosphorylated 5' end is complementary to the cohesive ends generated in step (a) of said double-stranded DNA fragment to yield 5' phosphorylated nucleotide sequences complementary to a sequence portion within said known sequence region of said DNA fragment, wherein said sequence portion is an annealing site for said 5' phosphorylated nucleotide sequences;
   (d) denaturing said 5' end-modified DNA fragment to produce single-stranded fragments containing said 5' phosphorylated nucleotide sequences;
   (e) intra-strand annealing of a 5' phosphorylated nucleotide sequence to said annealing site within said known sequence region of a single-stranded fragment, wherein said single-stranded fragment is a fragment containing said annealing site located downstream (3') to said unknown flanking sequence region, to form a single-stranded loop, or pan portion, with a double-stranded stem of an otherwise single-stranded handle, of a panhandle structure;
   (f) heat stable ligating an oligonucleotide primer 1, complementary to a known sequence region downstream (3') from said annealing site for said 5' phosphorylated nucleotide sequences, to the recessed 5' phosphorylated end of said double-stranded portion of said handle to elongate said double-stranded portion of said otherwise single-stranded handle of said panhandle structure;
   (g) performing a first stage polymerase amplification reaction using said oligonucleotide primer 1 annealing to said known sequence region downstream (3') from said annealing site for said 5' phosphorylated nucleotide sequences;
   (h) further performing a second stage polymerase chain reaction using an oligonucleotide primer 3 complementary to both a portion of said known sequence region complementary to primer 1 and a portion of said annealing site for said 5' phosphorylated nucleotide sequences; and
   (i) further performing a third stage polymerase chain reaction using an oligonucleotide primer complementary to said annealing site for said 5' phosphorylated nucleotide sequences.

13. The method of claim 12, wherein said double-stranded DNA is genomic.

14. The method of claim 12, wherein said region of known sequence is an insertion element and said region of unknown flanking DNA sequence to be retrieved is an integration site for said insertion element and flanking regions thereof.

15. The method of claim 14, wherein said insertion element is a viral insertion element or a transposon insertion element.

16. The method of claim 12, wherein said region of known sequence is a cDNA and said region of unknown flanking DNA sequence to be retrieved is from a 3' or 5' flanking region, intron-exon junction, or intron.

17. The method of claim 12, wherein said region of known sequence is a cloning vector arm and said region of unknown flanking DNA sequence to be retrieved is the cloned DNA sequence lying adjacent said arm.

18. The method of claim 17, wherein said cloning vector is a yeast artificial chromosome.

19. The method of claim 12, wherein the double-stranded DNA is known.

20. The method of claim 12, wherein the double-stranded DNA is a gene, disease marker, or pathogen.

21. A method for the amplification of an unknown DNA sequence that flanks a known DNA sequence, comprising the steps of:

(a) digesting a double-stranded DNA fragment with a restriction enzyme to yield 5' phosphorylated nucleotide overhang sequences, wherein said DNA fragment comprises a region of known DNA sequence and a region of unknown flanking DNA sequence to be amplified;

(b) annealing a 5' phosphorylated single-stranded oligonucleotide to a bridging-oligonucleotide to yield a double-stranded oligonucleotide with a phosphorylated 5' end;

(c) ligating said 5' phosphorylated single-stranded oligonucleotide of said double-stranded oligonucleotide whose non-phosphorylated 5' end is complementary to the cohesive ends generated in step (a) of said double-stranded DNA fragment to yield 5' phosphorylated nucleotide sequences complementary to a sequence portion within said known sequence region of said DNA fragment, wherein said sequence portion is an annealing site for said 5' phosphorylated nucleotide sequences;

(d) denaturing said 5' end-modified DNA fragment to produce single-stranded fragments containing said 5' phosphorylated nucleotide sequences;

(e) intra-strand annealing of a 5' phosphorylated nucleotide sequence to said annealing site within said known sequence region of a single-stranded fragment, wherein said single-stranded fragment is a fragment containing said annealing site located downstream (3') to said unknown flanking sequence region, to form a single-stranded loop, or pan portion, with a double-stranded stem of an otherwise single-stranded handle, of a panhandle structure;

(f) heat stable ligating an oligonucleotide primer 1, complementary to a known sequence region downstream (3') from said annealing site for said 5' phosphorylated nucleotide sequences, to the recessed 5' phosphorylated end of said double-stranded portion of said handle to elongate said double-stranded portion of said otherwise single-stranded handle of said panhandle structure;

(g) performing a first stage polymerase amplification reaction using said oligonucleotide primer 1 annealing to said known sequence region downstream (3') from said annealing site for said 5' phosphorylated nucleotide sequences; and (h) further performing a second stage polymerase chain reaction using an oligonucleotide primer complementary to said annealing site for said 5' phosphorylated nucleotide sequences.

22. The method of claim 21, wherein said double-stranded DNA is genomic.

23. The method of claim 21, wherein said region of known sequence is an insertion element and said region of unknown flanking DNA sequence to be retrieved is an integration site for said insertion element and flanking regions thereof.

24. The method of claim 23, wherein said insertion element is a viral insertion element or a transposon insertion element.

25. The method of claim 21, wherein said region of known sequence is a cDNA and said region of unknown flanking DNA sequence to be retrieved is from a 3' or 5' flanking region, intron-exon junction, or intron.

26. The method of claim 21, wherein said region of known sequence is a cloning vector arm and said region of unknown flanking DNA sequence to be retrieved is the cloned DNA sequence lying adjacent said arm.

27. The method of claim 21, wherein said cloning vector is a yeast artificial chromosome.

28. The method of claim 21, wherein said double-stranded DNA is known.

29. The method of claim 21, wherein said double-stranded DNA is a gene, disease marker, or pathogen.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

AGCTGCTTGA GCCCAGAC                                                           18

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CTAGGCTTGA GCCCAGAC                                                           18

( 2 ) INFORMATION FOR SEQ ID NO:3:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GTCCCTGCTA GGGCCGTCTG GGCTCAAGC                                    29

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CCTCTGCATG GTCTCTCGGG CGCTGGG                                     27

( 2 ) INFORMATION FOR SEQ ID NO:5:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

TGAGGTAATG CCAAAGACCT ACTACTCTGG GTGCCTGCCG C                    41

( 2 ) INFORMATION FOR SEQ ID NO:6:

( i ) SEQUENCE CHARACTERISTICS:

(A) LENGTH: 26 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:6:

TGGTCTCTCG GGCGCTGGGG TCCCTG                26

(2) INFORMATION FOR SEQ ID NO:7:

(i) SEQUENCE CHARACTERISTICS:
(A) LENGTH: 37 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:7:

CCCGCTCAAC CCTTTTTCTC TGACCTGCTG TGATGTC         37